United States Patent [19]

Znaiden et al.

[11] Patent Number: 5,536,499
[45] Date of Patent: * Jul. 16, 1996

[54] COSMETIC COMPOSITIONS FOR REDUCING OR PREVENTING SIGNS OF CELLULITE

[75] Inventors: Alexander P. Znaiden, Trumbull; Michael C. Cheney, Fairfield; Craig S. Slavtcheff, Cheshire, all of Conn.; Suk H. Cho, Bogota, N.J.

[73] Assignee: Chesebrough-Pond's USA Co., Division of Conopco, Inc., Greenwich, Conn.

[ * ] Notice: The portion of the term of this patent subsequent to Feb. 24, 2015, has been disclaimed.

[21] Appl. No.: 393,977

[22] Filed: Feb. 24, 1995

[51] Int. Cl.$^6$ .............................. A61K 7/00; A61K 7/48
[52] U.S. Cl. ............................. 424/401; 514/860
[58] Field of Search ................. 424/401, 195.1; 514/860

[56] References Cited

U.S. PATENT DOCUMENTS

| | | | |
|---|---|---|---|
| 4,234,599 | 11/1980 | Van Scott et al. | 424/279 |
| 4,424,234 | 1/1984 | Alderson et al. | 424/317 |
| 4,612,331 | 9/1986 | Barratt et al. | 514/558 |
| 4,684,522 | 8/1987 | Marissal et al. | 424/195.1 |
| 4,839,161 | 6/1989 | Bowser et al. | 424/59 |
| 5,015,634 | 5/1991 | Siren | 514/103 |
| 5,019,566 | 5/1991 | Siren | 514/103 |
| 5,023,248 | 6/1991 | Siren | 514/103 |
| 5,030,451 | 7/1991 | Trebosc et al. | 424/401 |
| 5,037,803 | 8/1991 | Gueyne et al. | 514/2 |
| 5,051,411 | 9/1991 | Siren | 514/103 |
| 5,051,449 | 9/1991 | Kligman | 514/559 |
| 5,059,594 | 10/1991 | Sawai et al. | 514/103 |
| 5,082,833 | 1/1992 | Shamsuddin | 514/143 |
| 5,091,193 | 2/1992 | Enjolras et al. | 424/642 |
| 5,116,605 | 5/1992 | Alt | 424/70 |
| 5,194,259 | 3/1993 | Soudant et al. | 424/401 |
| 5,211,956 | 5/1993 | Sawai et al. | 424/451 |
| 5,215,759 | 6/1993 | Mausner | 424/489 |
| 5,268,176 | 12/1993 | Znaiden et al. | 424/401 |
| 5,300,289 | 4/1994 | Garlich et al. | 424/54 |
| 5,362,494 | 11/1994 | Zysman et al. | 424/401 |
| 5,407,677 | 4/1995 | Tominaga et al. | 424/401 |

OTHER PUBLICATIONS

Abstract of FR 2 554 344—published May 10, 1985.
Abstract of DE 4 242 876—published Jun. 23, 1994.
Kligman, A., "Early Destructive Effect of Sunlight on Human Skin", *JAMA*, (Dec. 29, 1969), vol. 210, pp. 2377–2380.
Lavker, R., "Structural Alterations in Exposed and Unexposed Aged Skin", *Journal of Investigative Dermatology*, (1979), vol. 73, pp. 59–66.
Smith, J. et al., "Alterations in Human Dermal Connective Tissue with Age and Chronic Sun Damage", *Journal of Investigative Dermatology*, (1962), vol. 39, pp. 347–350.
Shuster, S. et al., "The Influence of Age and Sex on Skin Thickness, Skin Collagen and Density", *British Journal of Dermatology* (1975), vol. 93, pp. 639–643.
Griffiths, Christopher E., et al., "Restoration of Collagen Formation in Photodamaged Human Skin by Tretinoin (Retinoic Acid)", *The New England Journal of Medicine* (1993), vol. 329, pp. 530–535.
Chen, S. et al., "Effects of All–Trans Retinoic Acid on UVB–Irradiated and Non–Irradiated Hairless Mouse Skin", *Society for Investigative Dermatology*, (1992), vol. 98, pp. 248–254.
Nakagawa, et. al., "Long–Term Culture of Fibroblasts in Contracted Collagen Gels: Effects on Cell Growth and Biosythetic Activity", The Society for Investigative *Dermatology, Inc.*, (1989), vol. 93, pp. 792–798.
Jutley, J. K. et al., "Influence of Retinoic Acid and TGF–α on Dermal Fibroblast Proliferation and Collagen Production in Monolayer Cultures and Dermal Equivalents", *Matrix*, (1993), vol. 13, pp. 235–241.
Co–pending application Serial No. 08/393,979.
Co–pending application Serial No. 08/394,122.

*Primary Examiner*—Sallie M. Gardner
*Attorney, Agent, or Firm*—Rimma Mitelman

[57] ABSTRACT

The invention is directed to increasing the strength and firmness of the skin and reducing the signs of cellulite. The inventive method includes applying to the skin a composition that includes inositol phosphate, particularly phytic acid and its salts, in a cosmetically acceptable carrier.

5 Claims, No Drawings

COSMETIC COMPOSITIONS FOR REDUCING OR PREVENTING SIGNS OF CELLULITE

BACKGROUND OF THE INVENTION

1. Field of the Invention

The invention concerns a method for reducing or preventing signs of cellulite.

2. Background of the Invention

In recent years, cosmetic compositions which improve the appearance of skin have become popular with consumers. There is, at the present time, a demand for cosmetic compositions which reduce the appearance, i.e., the outward indications or signs, of cellulite.

Cellulite is a lay term describing the uneven texture of skin in specific areas of the female body, primarily the hips, thighs, and buttocks. The prevalence of cellulite is high, estimated between 50% and 80% of the female population. Virtually no cellulite has been observed in men with normal androgen levels. The severity of cellulite tends to worsen with obesity, although it is easily observable in women with a below average body mass index, as well as with age, although postmenopausal women report a reduction in cellulite.

Premenopausal females tend to store fat subcutaneously, primarily in the glutcal/thigh areas where cellulite is most common. The elevation in androgen levels postmenopausally resume in a dramatic shift in fat storage patterns. Fat is stored in the visceral and subcutaneous depots of the abdomen, more similar to male fat storage patterns, explaining the reduction in cellulite symptoms of postmenopausal women. Triglyceride is stored in individual adipocytes which are grouped into capillary rich lobules. Thin, vertical septa of connective tissue separate the lobules and tether the overlying superficial fascia to the underlying muscle.

The dimpling/bumpy appearance of cellulite is a result of the deformation of the aformenetioned lobules as a result of outward forces on the adipose tissue (e.g., muscle flexing resulting in a localized outward pressure, pull of gravity). These lobules are large (up to 1 cm wide) and easily protrude into the overlying dermis, causing a visible deformation on the surface of the skin that presents itself as cellulite. As the connective sepia run in the same direction as these outward forces, they can offer no counter force to keep the adipose from deforming into the dermis.

Net fat storage or removal within the adipocyte is dependent on a balance between uptake of dietary triglycerides circulating in the blood via chylomicrons and breakdown of stored triglyceride within the adipocyte and removal of free fatty acids for subsequent energy utilization. Lipolysis (breakdown of triglyceride within the adipocyte), occurs when hormone sensitive lipase (HSL) is activated. HSL activation requires phosphorylation via a cAMP (cyclic adenosine monophosphate) dependent protein kinase. As such, cAMP level is rate limiting to lipolysis. Net level of cAMP is a result of a balance between its enzymatic synthesis from adenosine triphosphate (ATP) via adenylate cyclase and its breakdown via phosphodiesterases. Adipocytes express both beta and alpha-2 receptors, which both activate and inactivate, respectively, adenylate cyclase.

Most cellulite treatments focus on lipolysis as the primary mode of action. Soudant et al. (U.S. Pat. No. 5,194,259) teach anti-cellulitis composition using an alpha-2 blocker, theoretically stimulating lipolysis. A number of patents cite use of xanthines (e.g., caffeine and derivatives) as phosphodiesterase inhibitors (French Patent No. 2,499,405; French Patent No. 2,554,344; Marissal et al., U.S. Pat. No. 4,684,522; Trebose et al., U.S. Pat. No, 5,030,451). Unfortunately, these products have not had great success in the marketplace, presumably due to poor efficacy. The art discussed above does not envision a method of reducing the appearance of cellulite by increasing the strength and firmness of epidermal and dermal layers of the skin, which in turn results in an increased support for the underlying tissue. Rather, the anti-cellulite art focuses on the treatment of cellute via lipolysis.

A wealth of literature surrounds the beneficial chemistry of inositol phosphate. Most of this literature focuses upon the medicinal aspects involving oral ingestion of the material. For instance, U.S. Pat. No. 5,051,411 (Siren) utilizes inositol phosphates to reduce the negative effects of ingested toxic metals such as lead, mercury, nickel and chromium to prevent or alleviate disorders based upon such metals. Typical disorders disclosed were immunodeficiency, hypertension and dermatitis. Related disclosures are found in U.S. Pat. No. 5,015,634 (Siren) directed at preventing or alleviating tissue damage and U.S. Pat. No. 5,019,566 (Siren) directed at treating an inflammatory condition, such as arthritis. U.S. Pat. No. 5,023,248 (Siren) describes methods for treating diabetes or its complications by administration of inositol triphosphate.

U.S. Pat. No. 5,082,833 (Shamsuddin) discloses a method for moderating the rate of cellular mitosis by treatment with inositol phosphates. Target diseases are leukemia, AIDS and fungal or protozoal infections.

U.S. Pat. No. 5,059,594 (Sawal et al.) reports the use of phytic acid and ferric ions in compositions directed at the removal of uraroma and body smell, detoxication, treatment of diabetes and hyperlipemia, remediation of erythrocyte flexibility and dysmnesia and the inhibition of the proliferation of fat cells.

A much smaller body of literature has suggested the use of inositol phosphates such as phytic acid in the cosmetics area. For instance, U.S. Pat. No. 5,116,605 (Alt) incorporates phytic acid with a variety of other substances into a composition for mitigating male pattern baldness and testosterone-induced acne. U.S. Pat. No. 5,268,176 (Znalden et al.) reports the use of phytic acid for topical treatment of telangiectasia, a dermatological condition commonly known as spider veins. DE 4 242 876 (Beiersdorf) discloses cosmetic compositions containing citric acid, blotin, and phytic acid as an anti-oxidant. A considerable number of disclosures are related to the use of phytic acid as a dental care product, among the more recent being U.S. Pat. No. 5,300,289 (Garlich et al.).

While it is evident from the foregoing that inositol phosphates are useful in a broad range of medical treatments, knowledge about their cosmetic activities is still at a formative stage.

Accordingly, it is an object of the present invention to describe new uses for inositol phosphates in the cosmetics area.

It is another object of the present invention to provide a method of reducing the signs of cellulite by applying to a cellulite-affected skin a composition containing a combination of an inositol phosphoric acid and an alpha hydroxy acid.

These and other objects of the invention will become more apparent from the detailed description and examples that follow.

SUMMARY OF THE INVENTION

A method is provided for reducing or preventing signs of cellulite which includes application onto the skin of inositol phosphates in a pharmaceutically acceptable carrier.

DETAILED DESCRIPTION OF THE INVENTION

Now it has been found that inositol phosphates have utility in increasing the strength and firmness of dermal and epidermal layers thus preventing or reducing signs of cellulite.

Accordingly, the method of the present invention requires a phosphate derivative of inositol, which may be one or a combination of a mono-, di-, tri-, tetra-, penta- or hexa-phosphate of inositol. Inositol is also known as 1,2,3,4,5,6-hexahydroxycyclohexane and 1,2,3,4,5,6-cyclohoxane-hexol. Most preferred is inositol hexaphosphate, otherwise known as phytic acid. Salts of phytic acid are also suitable, e.g., a water-soluble salt of phytic acid selected from the group consisting of alkali metal, alkaline earth metal, ammonium and $C_2$-$C_{12}$ alkanolammonium salts. For further descriptions of these phosphates, attention is drawn to U.S. Pat. No. 5,051,411, herein incorporated by reference. Amounts of these phosphates may range anywhere from about 0.5% to about 30%, preferably from about 0.75% to about 15%, optimally from about 0.75% to about 12% by weight of the total composition.

Compositions of the present invention will also contain a cosmetically acceptable carrier for the inositol phosphate. Amounts of the carrier may range from about 60% to about 99.9%, preferably from about 80 to 99.5% by weight of the total composition. Included among the cosmetically acceptable carriers are emollients, surfactants, humectants, powders and water.

In the preferred embodiment of the invention, a cosmetically acceptable vehicle is comprised either of water or of a water/solvent blend. The solvent is optimally chosen from propylene glycol, ethanol, butylene glycol, and polyethylene glycols of various molecular weights.

Vehicles other than water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 centistokes at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5% to 95%, preferably from 25% to 90% by weight of the composition.

The cosmetically acceptable vehicle will usually form from 5% to 99.9%, preferably from 25% to 80% by weight of the emulsion, and can, in the absence of other cosmetic adjuncts, form the balance of the composition.

Optional Skin Benefit Materials and Cosmetic Adjuncts

In a preferred method according to the present invention a xanthine is applied along with an inositol phosphate to the cellulite-affected skin. The term "xanthine" as used herein includes the following compounds:

xanthine (C5H4O2N4);

1,3-dimethyl xanthine (commonly known as "theophylline");

3,7-dimethyl xanthine (commonly known as "theobromine");

trimethyl xanthine (commonly known as "caffeine");

alloxantin;

paraxanthine;

heteroxanthine;

salts of the above mentioned compounds (e.g., ethylenediamine salts of theophylline);

and mixtures thereof.

The preferred xanthine employed in the inventive method is caffeine and/or theophylline due to their availability and optimum efficacy.

The xanthine is employed in the inventive method preferably in an amount of at least 0.05%, generally in the amount of from 0.05% to 20%, preferably in the amount of from 0.10% to 10%, optimally in the amount of from 0.5% to 3.0% by weight of the composition in order to maximize efficacy at optimum cost.

Another preferred ingredient employed in the inventive method is an alpha hydroxy acid. The presence of the alpha hydroxy acid facilitates the increase in the strength and firmness of dental and epidermal layers of the skin. The alpha hydroxy acid has the following general structure:

$R_2CHOHCOOR_1$ wherein $R_1$ and $R_2$ are H, alkyl, arylalkyl or aryl, straight or branched chain or cyclic form, having 1 to 20 carbon atoms, and in addition $R_2$ may carry OH, CHO, COOH and alkoxy group having 1 to 9 carton atoms.

The typical alkyl, aralkyl and aryl groups for $R_1$ and $R_2$ include methyl, ethyl, propyl, isopropyl, butyl, pentyl, octyl, lauryl, stearyl, benzyl and phenyl, etc.

Examples of suitable alpha hydroxy acids include but are not limited to:

alpha hydroxy acetic acid (also known as "glycolic acid")

alpha hydroxybenzeneacetic acid (also known as "mandelic acid")

alpha hydroxypropionic acid (also known as "lactic acid")

alpha hydroxybutanoic acid alpha hydroxyhexanoic acid alpha hydroxyoctanoic acid (also known as "alpha hydroxy caprylic acid")

alpha hydroxynonanoic acid alpha hydroxydecanoic acid alpha hydroxyundecanoic acid alpha hydroxydodecanoic acid (also known as "alpha hydroxy lauric acid")

alpha hydroxytetradecanoic acid alpha hydroxyhexadecanoic acid alpha hydroxyoctadecanoic acid alpha hydroxyoctaeicosanoic acid;

dicarboxylic alpha hydroxy acids:

dihydroxybutanedioic acid (tartaric acid)

2-hydroxybutanedioic acid (malic acid)

2-hydroxy propanedioic acid 2-hydroxy hexanedioic acid 2-hydroxy octanedioic acid 2-hydroxy decanedioic acid 2-hydroxy dodecanedioic acid 2-hydroxy myristicdioic acid 2-hydroxy palmiticdioic acid Tricarboxylic alpha hydroxy acids:

2-hydroxy-1,2,3,-propanetricarboxylic acid (citric acid)

1-hydroxy-1,2,3,-propanetricarboxylic acid (isocitric acid)

and mixtures thereof.

Salts of alpha hydroxy acids (e.g., potassium, sodium, ammonium, triethanolammonium salts) are also meant to be included within the term "alpha hydroxy acid". Depending on the pH of the composition, a mixture of the salt and the acid is present.

The preferred alpha hydroxy acids are monocarboxylic acids, in order to improve skin penetration and efficacy.

Even more preferably, the hydroxy acid is chosen from lactic acid, glycolic acid, mandelic acid, and mixtures thereof to optimize the efficacy of compositions by increasing percutaneous absorption. In the most preferred embodiment of the invention, in order to maximize the performance of hydroxy acid, inventive compositions contain the L-form of an alpha hydroxy acid.

Preferably the amount of the alpha hydroxy acid component present in the composition according to the invention is from 1.5% to 20%, more preferably from 1.5% to 15%, and most preferably from 3.0% to 12.0% by weight of the composition.

An oil or oily material may be present, together with an emulsifier to provide either a water-in-oil emulsion or an oil-in-water emulsion, depending largely on the average hydrophilic-lipophilic balance (HLB) of the emulsifier employed.

Various types of active ingredients may be employed in the method of the present invention. Actives are defined as skin benefit agents other than emollients and other than ingredients that merely improve the physical characteristics of the composition. Although not limited to this category, general examples include sunscreens, tanning agents, skin anti-wrinkling agents, anti-inflammatory agents, skin lighteners and moisturizers.

Sunscreens include those materials commonly employed to block ultraviolet light. Illustrative compounds are the derivatives of PABA, and cinnamate. For example, octyl methoxycinnamate and 2-hydroxy-4-methoxy benzophenone (also known as oxybenzone) can be used. Octyl methoxy-cinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Suitable anti-inflammatory compounds include but are not limited to rosmarinic acid, glycyrrizinate derivatives, alpha bisabolol, azulene and derivatives thereof, asiaticoside, sericoside, ruscogenin, escin, escolin, quercetin, rutin, betulinic acid and derivatives thereof, catechin and derivatives thereof.

Suitable vasoactive compounds include but are not limited to papaverine, yohimbine, visnadin, khellin, bebellin, nicotinate derivatives.

Suitable skin whitening compounds include but are not limited to ferulic acid and/or kojic acid.

Anti-wrinkling compounds include but are not limited to alpha hydroxy acids, retinol and derivatives, tocopherol and derivatives, salicylates and derivatives.

Surfactants, which are also sometimes designated as emulsifiers, may be incorporated into the cosmetic compositions of the present invention. Surfactants can comprise anywhere from about 0.5% to about 30%, preferably from about 1% to about 15% by weight of the total composition. Surfactants may be cationic, nonionic, anionic, or amphoteric in nature and combinations thereof may be employed.

Illustrative of the nonionic surfactants are alkoxylated compounds based upon fatty alcohols, fatty acids and sorbitan. These materials are available, for instance, from the Shell Chemical Company under the "Neadol" designation. Copolymers of polyoxypropylene-polyoxyethylene, available under the Pluronic trademark sold by The BASF Corporation, are sometimes also useful. Alkyl polyglycosides available from the Henkel Corporation similarly can be utilized for the purposes of this invention.

Anionic-type surfactants may include fatty acid soaps, sodium lauryl sulphate, sodium lauryl ether sulphate, alkyl benzene sulphonate, mono and/or dialkyl phosphates and sodium fatty acyl isethionate.

Amphoteric surfactants include such materials as dialkylamine oxide and various types of betaines (such as cocoamido propyl betaine).

Emollients are often incorporated into cosmetic compositions of the present invention. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1% to 20% by weight, preferably from about 0.5% to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust bean gum. Under certain circumstances the thickening function may be accomplished by a material also serving as a silicone or emollient. For instance, silicone gums in excess of 10 centistokes and esters such as glycerol stearate have dual functionality. Cellulosic derivatives may also be employed, e.g., hydroxypropyl cellulose (Klucel Hi®).

Many cosmetic compositions, especially those containing water, must be protected against the growth of potentially harmful microorganisms. Preservatives are, therefore, necessary. Suitable preservatives include alkyl esters of p-hydroxybenzoic acid, hydantoin derivatives, proplonate salts, and a variety of quaternary ammonium compounds.

Particularly preferred preservatives of this invention are methyl paraben, propyl paraben, imidazolidinyl urea, sodium dehydroxyacetate and benzyl alcohol. Preservatives will usually be employed in amounts ranging from about 0.5% to 2% by weight of the composition.

Powders may be incorporated into the cosmetic composition employed in the invention. These powders include chalk, talc, Fullers earth, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these materials may range anywhere from 0.001% up to 20% by weight of the composition.

Preferably, the pH of the composition employed in the present invention is 5.5 or below, preferably in the range of from 1.5 to 5.5, to maximize the benefits obtained as the result of the inventive method.

The method of the present invention is useful for reducing or preventing the appearance of cellulite, for improving the firmness and elasticity of skin and generally to enhance the quality and flexibility of skin.

The following examples will more fully illustrate the embodiments of this invention, but the invention is not limited thereto. All parts, percentages and proportions referred to herein and in the appended claims are by weight unless otherwise indicated.

EXAMPLE 1

Collagen, the predominant matrix skin protein, is known to impart tensile strength to skin. It has been shown that collagen is significantly reduced with age and UV exposure. The degradation or destruction of the architecture of these proteins decreases the tensile strength of the skin causing wrinkles and laxity. Many studies involving human subjects have shown that collagen type I is decreased with increasing severity of photodamage (See Kilgman, A., *JAMA*, (1969), 210, pp. 2377–2380; Lavker. R., *J. Inv. Derm.*, (1979), 73, 79–66; Smith. J. et al., *J. Inv. Derm.*, (1962), 39, pp. 347–350; and Shuster, S. et al., *Br. J. Dermatol.*, (1975), 93, pp. 639–643); and some correlation in the histology of wrinkles and reduction in collagen levels in the sun-exposed skin has been reported. See Chen, S.; Kiss, I., J. Inv. Derm., (1992), 98, 975–978. Voorhees and collegues have supported these findings by showing the restoration of collagen type I in photodamaged human skin by a topical treatment with tretinoin. See Christopher, E., et al., The New Eng. Jou. of Medicine (1993), 329, pp. 530–535. These results provide the first in vive evidence that retinoic acid restores collagen type I. Many etiology studies showed a parallel effect between collagen synthesis and wrinkle effacement. It is also believed that the strengthening of the dermal matrix by collagen stimulation may have some beneficial effect for treatment of cellulite. See U.S. Pat. No. 5,051,449 (Kilgman).

Materials and Methods

The protocol outlined by Nakagawa, et. al., *J. Inv. Derm.*, (1989), 93, pp. 792–798, and Jutley, J. K. et al., *Matrix*, (1993) 13, pp. 235–241, was followed quite closely with a few minor modifications made along the way. The culture media were from GIBCO, and the plastic culture dishes were from Costar, Human dermal fibreblasts (Clonetics or ATCC) were cultured in a Minimum Essential Medium (MEM)+ 10% Fetal Bovine Serum (FBS). Typically, the experiments were performed on the sixth to ninth passages. Dermal equivalents were prepared using Vitrogen 100 (purified, pepsin-solubilized bovine dermal collagen) from Celtrix Corp. The fibreblasts were mixed with neutralized collagen to give a final concentration or $2.5 \times 10^5$ cells/mL and 1.5 mg/mL of gel. The mixture was then seeded in non-treated 96-well plates in aliquot of 100 ml/well. The gels were allowed to polymerize for 60 minutes at 37° C., then the MEM+10% FBS was added to each well in 100 µg/mL aliquot. The sterility of the cultures was checked regularly, and the cell humeration was performed using routine techniques.

Incubations

Cells were incubated at 37° C. for 24 hours in a 5% $CO_2$ and 95% air atmosphere. After 24 hours, the cultures were given fresh MEM without FBS and 50 µg/mL ascorbic acid and phytic acid. The test dishes were supplemented with two concentration of phytic acid. Transforming growth factor-B1 (TGFβ) at 10 µg/mL was used as the positive control for the collagen assay. After additional day of incubation, the cultures were given 20 mCi/mL of (2,3-$^3$H) proline and fresh ascorbic acid at 50 mg/mL. The test plates were then further incubated for 24 hours.

Measuring Collagen and Protein Synthesis

At the end of the incubation period, the gels were dissolved using 100 mL of 50 mM HCl and heated at 37° C. for 60 minutes or until the gel was completely dissolved. After neutralization with NaOH, the samples were transferred from the original culture plates to round bottom, high protein binding Elisa 96-well plates (Corning). The samples were splitted, and a buffer containing Tris-HCl (120 mM, at pH 7.2) and calcium acetate (24 mM) was added to each sample, bringing the total volume up to 150 mL. Other half of the samples were treated with bacterial collagenase (Worthington) and a buffer, and bath sets of samples were left at room temperature for 18–24 hours. Bovine serum albumin (BSA)(3 mg/mL) was added to the samples to act as a carrier protein. Then the samples were precipitated at 4° C. for 30 minutes in the presence of 10% trichloroacetic acid (TCA) and centrifuged at 2750 RPMs for 10 minutes. Two more washes in 5% TCA were performed, and the final pellets were dissolved in 100 mL of 0.1M NaOH for 60 minutes at 50° C. The 100 mL samples were added to 5mL of scintiverse and counted on a Beckman scintillator. The percentage of new collagen synthesis was calculated using the formula similar to that described by Martens et al. The equation is as follows:

$$\% \text{ collagen} = 100\% \times (b-c/c \times 5.4 + (b-c))$$

where b=total proline incorporated; C=total proline incorporated without collagen.

The data was then further equated for relative comparison with control, and the equation is as follows:

Total Collagen increase=avg. total proline incorporation (active)×
relative % collagen increase calculated from above equation/
avg. total proline (control)×relative % collagen increase from
above equation.

The stimulating activity on collagen synthesis by a fibroblast culture treated with an inositol phosphate (phytic acid) was investigated. Phytic acid was purchased from Aldrich Chemicals. Phytic acid at various concentrations was tested in a dermal equivalent assay. In order to normalize the results, each experiment was compared to the control. The results that were obtained are summarized in Table 1.

TABLE 1

THE EFFECT OF PHYTIC ACID ON COLLAGEN SYNTHESIS

| Experiment Number: | Total Protein | Non Collagen Protein | Percent Collagen Synthesis | Percent increase compare to Control |
|---|---|---|---|---|
| Exp 1: | 26256 ± | 21500 ± | 4.01 ± | — |
| Control | 768 | 1856 | 1.5 | |
| Phytic acid @ 0.001% | 27054 ± 1228 | 23143 ± 811 | 3.03 ± 0.77 | ≅78% |
| Phytic acid @ 0.005% | 27167 ± 1520 | 19763 ± 1476 | 6.53 ±* 1.31 | ≈168% |

*P < 0.03

The increase at 0.005% was statistically significant compared to control.

EXAMPLE 2

Formula A–C summarized in Table 2 below are typical compositions employed in the inventive method.

| INGREDIENT | A | B | C |
|---|---|---|---|
| Phytic acid | 5 | 8 | 16 |
| Stearic acid | 2.20 | 2.20 | 2.20 |
| PPG-2 myristyl ether propionate | 1.5 | 1.6 | 1.5 |
| PEG-100 stearate | 1.2 | 1.2 | 1.20 |
| TEA | 1.34 | 1.34 | 1.34 |
| butylene glycol | 2.5 | 2.5 | 2.5 |
| isostearyl palmitate | 1.0 | 1.0 | 1.0 |
| isobutyl stearate | 1.0 | 1.0 | 1.0 |
| glyceryl hydroxystearate | 0.9 | 0.9 | 0.9 |
| sorbitan stearate | 0.50 | 0.50 | 0.50 |
| cetearyl alcohol | 0.50 | 0.50 | 0.50 |
| tributyl citrate | 0.50 | 0.50 | 0.50 |
| soya sterols | 0.50 | 0.50 | 0.50 |
| caffeine | 0.50 | 0.50 | 0.50 |
| ginkgo biloba extract | 0.50 | 0.50 | 0.50 |

-continued

| INGREDIENT | A | B | C |
|---|---|---|---|
| silver birch extract | 0.50 | 0.50 | 0.50 |
| angelica extract | 0.50 | 0.50 | 0.50 |
| sepigel | 0.50 | 0.50 | 0.50 |
| DC-200, 50 cbts dmirthicone | 0.30 | 0.30 | 0.30 |
| myreth-3-myristate | 0.30 | 0.30 | 0.30 |
| aluminum magnesium silicate | 0.40 | 0.40 | 0.40 |
| xanthan gum | 0.30 | 0.30 | 0.30 |
| vitamin E acetate | 0.20 | 0.20 | 0.20 |
| green tea extract (86% theophylline) | 0.20 | 0.20 | 0.20 |
| vitamin A palmitate | 0.20 | 0.20 | 0.20 |
| hydroxycaprylic acid | 0.10 | 0.10 | 0.10 |
| propyl paraben | 0.10 | 0.10 | 0.10 |
| methyl paroben | 0.15 | 0.15 | 0.15 |
| escin | 0.10 | 0.10 | 0.10 |
| dipotassium glycyrlizinate | 0.10 | 0.10 | 0.10 |
| alpha bisabolol | 0.10 | 0.10 | 0.10 |
| BMT | 0.05 | 0.05 | 0.05 |
| Disodium EDTA | 0.05 | 0.05 | 0.05 |
| Aslaticoside | 0.01 | 0.01 | 0.01 |
| Soticoside | 0.01 | 0.01 | 0.01 |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A method for enhancing collagen synthesis and thereby reducing signs of cellulite, the method comprising topically applying to the skin a cosmetic composition comprising from about 0.5% to about 30% by weight of an inositol phosphate and from about 70% to about 99.5% by weight of a cosmetically acceptable carrier.

2. A method according to claim 1 wherein the inositol phosphate is phytic acid.

3. A method according to claim 1 wherein the inositol phosphate is a water-soluble salt of phytic acid selected from the group consisting of alkali metal, alkaline earth metal, ammonium and $C_2$–$C_{12}$ alkanolammonium salts.

4. A method according to claim 1 further comprising applying to the skin a xanthine.

5. A method according to claim 1 further comprising applying to the skin an alpha hydroxy acid.

* * * * *